US 7,651,459 B2

(12) United States Patent
Cameron et al.

(10) Patent No.: US 7,651,459 B2
(45) Date of Patent: Jan. 26, 2010

(54) METHOD AND APPARATUS FOR COIL POSITIONING FOR TMS STUDIES

(75) Inventors: Allan Cameron, Natick, MA (US); John A. MacNeill, Melrose, MA (US); Gregg Flender, Bedford, MA (US); Mark Edward Riehl, Doylestown, PA (US)

(73) Assignee: Neuronetics, Inc., Malvern, PA (US)

( * ) Notice: Subject to any disclaimer, the term of this patent is extended or adjusted under 35 U.S.C. 154(b) by 429 days.

(21) Appl. No.: 10/752,164

(22) Filed: Jan. 6, 2004

(65) Prior Publication Data
US 2005/0148808 A1    Jul. 7, 2005

(51) Int. Cl.
*A61N 2/00* (2006.01)
(52) U.S. Cl. .......................................................... 600/9
(58) Field of Classification Search ............... 600/9–15, 600/429, 415, 427, 417, 424, 411; 606/130; 128/897
See application file for complete search history.

(56) References Cited

U.S. PATENT DOCUMENTS

| | | | |
|---|---|---|---|
| 3,683,923 A | 8/1972 | Anderson | |
| 4,712,558 A | 12/1987 | Kidd et al. | |
| 4,995,395 A | 2/1991 | Ilmoniemi et al. | |
| 5,097,833 A | 3/1992 | Campos | 128/421 |
| 5,116,304 A | 5/1992 | Cadwell | |
| 5,299,569 A | 4/1994 | Wernicke et al. | 607/45 |
| 5,370,117 A * | 12/1994 | McLaurin, Jr. | 5/622 |

(Continued)

FOREIGN PATENT DOCUMENTS

EP    0 998 958 A3    5/2000

(Continued)

OTHER PUBLICATIONS

Baudewig, J. et al., "Functional MRI of Cortical Activations Induced by Transcranial Magnetic Stimulation(TMS)", *Brain Imaging-NeuroReport*, 2001, 12(16), 3543-3548.

(Continued)

*Primary Examiner*—Charles A Marmor, II
*Assistant Examiner*—Christine D Hopkins
(74) *Attorney, Agent, or Firm*—Woodcock Washburn LLP (57) ABSTRACT

A device provides simple positioning of the patient's head and simple positioning of the TMS coil relative to a coordinate system of the patient's head once the head is positioned. The TMS coil is fixed at a treatment position in the coordinate system of the patient's head and the position in the coordinate system is recorded for use in subsequent clinical sessions. A positioner assembly supports the weight of the TMS coil and allows the operator to freely move the TMS coil to search for the patient's motor threshold position (MTP) and/or the treatment position (TXP). If the TXP is in registration with the MTP, once the MTP is determined, the positioner assembly requires only a single adjustment of the magnet position to locate the TXP where the coil is locked in place for the duration of the TMS therapy. By recording the positions of the different adjustable components in the respective coordinate directions of the coordinate system of the patient's head, exact repositioning of the TMS coil for the patient during a subsequent clinical visit is made possible without use of expensive imaging equipment.

45 Claims, 5 Drawing Sheets

U.S. PATENT DOCUMENTS

| | | | |
|---|---|---|---|
| 5,655,534 A | 8/1997 | Ilmoniemi | 128/653.1 |
| 5,707,334 A | 1/1998 | Young | |
| 5,769,778 A | 6/1998 | Abrams et al. | |
| 5,813,970 A | 9/1998 | Abrams et al. | |
| 5,828,770 A | 10/1998 | Leis et al. | 382/103 |
| 5,855,582 A * | 1/1999 | Gildenberg | 606/130 |
| 5,923,417 A | 7/1999 | Leis | 356/141.1 |
| 6,061,644 A | 5/2000 | Leis | 702/153 |
| 6,066,084 A | 5/2000 | Edrich et al. | |
| 6,117,066 A | 9/2000 | Abrams et al. | |
| 6,169,963 B1 | 1/2001 | Markov | |
| 6,179,771 B1 | 1/2001 | Mueller | 600/13 |
| 6,198,958 B1 | 3/2001 | Ives et al. | |
| 6,253,109 B1 | 6/2001 | Gielen | |
| 6,256,531 B1 | 7/2001 | Ilmoniemi et al. | 600/544 |
| 6,288,785 B1 | 9/2001 | Frantz et al. | 356/614 |
| 6,366,814 B1 | 4/2002 | Boveja et al. | |
| 6,389,318 B1 | 5/2002 | Zarinetchi et al. | 607/61 |
| 6,402,678 B1 | 6/2002 | Fischell et al. | |
| 6,418,345 B1 * | 7/2002 | Tepper et al. | 607/51 |
| 6,463,328 B1 | 10/2002 | John | 607/45 |
| 6,480,743 B1 | 11/2002 | Kirkpatrick et al. | |
| 6,484,059 B2 | 11/2002 | Gielen | 607/45 |
| 6,488,617 B1 | 12/2002 | Katz | |
| 6,497,648 B1 | 12/2002 | Rey | 600/14 |
| 6,503,187 B1 | 1/2003 | Ilmoniemi et al. | |
| 6,516,213 B1 | 2/2003 | Nevo | 600/424 |
| 6,516,288 B2 | 2/2003 | Bagne | 702/179 |
| 6,537,197 B1 | 3/2003 | Ruohonen et al. | 600/13 |
| 6,551,233 B2 | 4/2003 | Perreault et al. | 600/9 |
| 6,553,326 B1 | 4/2003 | Kirsch et al. | 702/65 |
| 6,560,490 B2 | 5/2003 | Grill et al. | 607/72 |
| 6,567,702 B1 | 5/2003 | Nekhendzy et al. | |
| 6,571,123 B2 | 5/2003 | Ives et al. | 600/544 |
| 6,572,528 B2 | 6/2003 | Rohan et al. | |
| 6,625,563 B2 | 9/2003 | Kirsch et al. | 702/150 |
| 6,827,681 B2 | 12/2004 | Tanner et al. | 600/9 |
| 6,849,040 B2 | 2/2005 | Ruohonen et al. | 600/14 |
| 6,978,179 B1 | 12/2005 | Flagg et al. | |
| 2002/0013612 A1 | 1/2002 | Whitehurst | |
| 2002/0087201 A1 | 7/2002 | Firlik et al. | 607/45 |
| 2002/0091419 A1 | 7/2002 | Firlik et al. | 607/45 |
| 2002/0103515 A1 | 8/2002 | Davey et al. | |
| 2002/0123780 A1 | 9/2002 | Grill et al. | |
| 2002/0160436 A1 | 10/2002 | Markov et al. | |
| 2002/0169355 A1 | 11/2002 | Rohan et al. | |
| 2003/0004392 A1 | 1/2003 | Tanner et al. | 600/9 |
| 2003/0023159 A1 | 1/2003 | Tanner | 600/417 |
| 2003/0028072 A1 | 2/2003 | Fischell | 600/13 |
| 2003/0050527 A1 | 3/2003 | Fox et al. | 600/13 |
| 2003/0065243 A1 | 4/2003 | Tanner | 600/9 |
| 2003/0073899 A1 | 4/2003 | Ruohonen et al. | 600/417 |
| 2003/0074032 A1 | 4/2003 | Gliner et al. | |
| 2003/0082507 A1 | 5/2003 | Stypulkowski | 434/262 |
| 2003/0088274 A1 | 5/2003 | Gliner et al. | 607/3 |
| 2003/0097161 A1 | 5/2003 | Firlik et al. | 607/72 |
| 2003/0125786 A1 | 7/2003 | Gliner et al. | 607/116 |
| 2003/0130706 A1 | 7/2003 | Sheffield et al. | 607/46 |
| 2004/0010177 A1 | 1/2004 | Rohan et al. | |
| 2004/0019370 A1 | 1/2004 | Gliner et al. | 607/48 |
| 2004/0077921 A1 | 4/2004 | Becker et al. | 600/9 |
| 2004/0127942 A1 | 7/2004 | Yomtov et al. | |
| 2004/0153129 A1 | 8/2004 | Pless et al. | 607/62 |
| 2005/0021104 A1 | 1/2005 | DiLorenzo | 607/45 |
| 2005/0049486 A1 * | 3/2005 | Urquhart et al. | 600/429 |
| 2005/0124848 A1 | 6/2005 | Holzner | |
| 2005/0216071 A1 | 9/2005 | Devlin et al. | |
| 2005/0228209 A1 | 10/2005 | Schneider et al. | 600/13 |
| 2005/0256539 A1 | 11/2005 | George et al. | |

FOREIGN PATENT DOCUMENTS

| | | |
|---|---|---|
| EP | 1 273 320 A1 | 1/2003 |
| WO | WO 99/64884 | 12/1999 |
| WO | WO 00/74777 A1 | 12/2000 |
| WO | WO 01/12236 A2 | 2/2001 |
| WO | WO 01/28622 A2 | 4/2001 |
| WO | WO 01/97906 A2 | 12/2001 |
| WO | WO 02/09811 A1 | 2/2002 |
| WO | WO 02/31604 A2 | 4/2002 |
| WO | WO 02/32504 A2 | 4/2002 |
| WO | WO 02/072194 A2 | 9/2002 |
| WO | WO 02/008545 A1 | 10/2002 |
| WO | WO 02/085449 A2 | 10/2002 |
| WO | WO 02/089902 A2 | 11/2002 |
| WO | WO 02/094997 A2 | 11/2002 |
| WO | WO 03/035163 | 5/2003 |
| WO | WO 03/090604 A2 | 11/2003 |
| WO | WO 03/098268 A1 | 11/2003 |
| WO | WO 2004/100765 A2 | 11/2004 |
| WO | WO 2005/000401 A1 | 1/2005 |
| WO | WO 2005/065768 A1 | 7/2005 |
| WO | WO 2005/067610 A2 | 7/2005 |

OTHER PUBLICATIONS

Bohning, D.E. Ph.D. et al., "BOLD-fMRI Response to Single-Pulse Transcranial Magnetic Stimulation (TMS)", *Journal of Magnetic Resonance Imaging*, 2000, 11, 569-574.

Bohning, D.E. Ph.D. et al., "A Combined TMS/fMRI Study of Intensity-Dependant TMS over Motor Cortex", *Society of Biological Psychiatry*, 1999, 45, 385-394.

Bohning, D.E. et al., "A TMS Coil Positioning/Holding System for MR Image-Guided TMS Interleaved with fMRI", *Clinical Neurophysiology*, 2003, 114, 2210-2219.

George, M.S. et al., "A Controlled Trial of Daily Left Prefrontal Cortex TMS for Treating Depression", *Society of Biological Psychiatry*, 2000, 48, 962-970.

Grafman, J. Ph.D., "TMS as a Primary Brain Mapping Tool" *Transcranial Magnetic Stimulation in Neuropsychiatry*, 2000, 115-140.

Lisanby, S.H. et al., "Sham TMS: Intracerebral Measurement of the Induced Electrical Field and the Induction of Motor-Evoked Potentials", *Society of Biological Psychiatry*, 2001, 49, 460-463.

Lorberbaum, J.P., M.D. et al., "Safety Concerns of TMS", *Transcranial Magnetic Stimulation in Neuropsychiatry*, 2000, 141-161.

Loo, C.K. et al., "Transcranial Magnetic Stimulation (TMS) in Controlled Treatment Studies: Are Some "Sham" Forms Active?", *Society of Biological Psychiatry*, 2000, 47, 325-331.

Nahas, Z. et al., "Left Prefrontal Transcranial Magnetic Stimulation(TMS) Treatment of Depression in Bipolar Affective Disorder: A Pilot Study of Acute Safety and Efficacy", *Bipolar Disorders*, 2003, 5, 40-47.

Nahas, Z. et al., "Unilateral Left Prefrontal Transcranial Magnetic Stimulation(TMS) Produces Intensity-Dependent Bilateral Effects as Measured by Interleaved BOLD fMRI", *Society of Biological Psychiatry*, 2001, 50, 712-720.

Pridmore, S., "Substitution of Rapid Transcranial Magnetic Stimulation Treatments for Electroconvulsive Therapy Treatments in a Course of Electroconvulsive Therapy", *Depression and Anxiety*, 2000, 12, 118-123.

Ruohonen, J., "Electroencephalography Combined with TMS", BioMag Laboratory, Helsinki University Central Hospital, http://www.biomag.helsinki.fi/tms/TMSEEG.html, Oct. 6, 1999, 22 pages.

* cited by examiner

METHOD AND APPARATUS FOR COIL POSITIONING FOR TMS STUDIES

FIELD OF THE INVENTION

The present invention relates to a method and apparatus for precisely positioning a medical instrument with respect to a patient and, more particularly, to a positioning system and method for precisely and repeatably positioning a transcranial magnetic stimulation coil at the treatment position of a patient.

BACKGROUND OF THE INVENTION

Current methods of placement and positioning of coils for Transcranial Magnetic Stimulation (TMS) studies are either manual methods or approaches designed for research that require expensive and complex imaging or computational systems to determine three dimensional spatial coordinates for positioning reference. These techniques have severe clinical limitations. The manual methods do not provide a convenient means for repeated and accurate placement, while the three dimensional spatial methods based on imaging modalities are expensive, time consuming, and not conducive to clinical use. A positioning technique for clinical use is desired that provides a simple way for the operator to perform repeated and accurate coil placement for TMS studies and treatments in a time-efficient and inexpensive manner.

Manual Methods

In accordance with the conventional manual placement and position marking technique, a treatment position on the patient's head or a position used to find a treatment position, such as the patient's motor threshold position (MTP), is determined by moving the coil near a predicted area determined by patient anatomical landmarks until the desired motor response is achieved. The position is marked, for example, with an ink mark on the patient's head. In the case of using the TMS coil for treatment of depression, for example, the TMS therapy position is determined by moving the coil from the MTP along a line in the anterior direction a prescribed distance (a widely accepted distance is 5 cm). The Therapy Position (TXP) is then marked on the patient (e.g., with ink) so it can be easily found in subsequent therapy sessions.

The most common method of localization used for TMS studies is described by George et al. in "Daily Repetitive Transcranial Magnetic Stimulation (rTMS) Improves Mood in Depression," NeuroReport, Vol. 6, No. 14, October 1995, pp. 1853-1856, and by Pascual-Leone et al. in "Rapid-Rate Transcranial Magnetic Stimulation of Left Dorsolateral Prefrontal Cortex in Drug-Resistant Depression," The Lancet, Vol. 348, Jul. 27, 1996, pp. 233-237. Simply stated, in these methods the coil is first moved over the area of the left motor cortex until stimulation of the contralateral abductor pollicis brevis muscle (APB) is attained. This position is the motor threshold position (MTP) and is typically located on a line between the left auditory meatus (i.e. ear canal) and the vertex of the head, at a point about ½ to ⅔ of the distance to the vertex. In the case of excitatory stimulation of the left prefrontal cortex for the treatment of depression, for example, the TXP is located by starting at the MTP and moving 5 cm toward the midpoint between the tip of the nose and the nasion (protuberance just above the bridge of the nose). More details of techniques for determining the MTP are also described in related U.S. patent application Ser. No. 10/714,741, filed Nov. 17, 2003, the contents of which are incorporated herein by reference.

The shortcomings of such manual methods are that precisely determining the line from the MTP to the TXP is difficult, marks applied to the patient either wash off between treatment sessions (so they do not help with the next treatment session) or they do not wash off (which is cosmetically undesirable), the coil may not be comfortably held at the TXP throughout a therapy session, and the technique is highly operator dependent and not conducive to repeatable and accurate positioning.

The problem of applying marks to the patient has been addressed in the art by applying a swim cap or similar conformal headgear to the patient and marking the headgear rather than the patient. Of course, this approach requires careful registration of the headgear during subsequent therapy sessions, which is crude, imprecise, and highly operator dependent. Moreover, such an approach still requires accurate coil placement and a mechanism for holding the coil in place.

Complex Imaging/Computational Systems

The Brainsight™ System developed by Rogue Research, Inc. of Montreal, Canada and distributed by Magstim is complex and is designed primarily for research purposes. This system uses diagnostic images from MRI or PET systems to determine the spatial relationship between internal anatomy and external landmarks and then aligns to the external landmark for therapy or other studies requiring accurate localization. While this approach is useful for research purposes, it is highly impractical and complex and is thus not usable in general clinical practice. Moreover, such techniques have generally been used to overlay coordinate systems onto images and not for identifying particular treatment positions for specific therapies.

Robotic Arms for Holding TMS Coils

U.S. Pat. No. 6,266,556 and U.S. Patent Application No. 2003/0050527 include descriptions of methods in which a robotic arm is operatively coupled to the TMS coil for positioning the coil with respect to the patient and holding the coil in place during TMS treatment. A similar technique using a robotic arm for coil placement is also disclosed in U.S. Patent Application Nos. 2003/0004392 to Tanner et al. and 2003/0065243 to Tanner. These applications further disclose a technique for modeling the spatial structure of the patient's brain for determining the proper stimulation position using a stimulation model. While these techniques provide controlled movement and placement of the coil, they are quite expensive and do not provide for repeatable placement of the coil with respect to a particular patient's head in a clinical setting. As a result, the manual and/or complex imaging techniques described above must also be used for placement of the coil with respect to the patient.

Thus, the need for a simple, cost-effective and intuitive way to accurately and repeatably position the coil for TMS therapy in a clinical setting has not been met in the prior art. The present invention addresses this need.

SUMMARY OF THE INVENTION

The invention addresses the above-mentioned limitations in the prior art through use of a mechanical device that provides simple positioning of the patient's head and simple positioning of the TMS coil relative to a coordinate system of the patient's head once the head is positioned. The TMS coil is fixed at a treatment position in the coordinate system of the patient's head and the position in the coordinate system is recorded for use in subsequent clinical sessions. In an exemplary embodiment, the positioner assembly is a mechanical system that supports the weight of the TMS coil (approximately five pounds in the case of designs that use a ferromagnetic core material) and allows the operator to freely move the TMS coil to search for the treatment position and/or the patient's motor threshold position (MTP). Once the MTP is determined, the positioner assembly requires only a single adjustment of the magnet position to locate the treatment position (TXP) where the coil is locked in place for the duration of the TMS therapy. By recording the positions of the different adjustable components in the respective coordinate directions of the coordinate system of the patient's head, exact repositioning of the TMS coil for the patient during a subsequent clinical visit is made possible without use of expensive imaging equipment. Exemplary embodiments described herein illustrate a device for repeatably positioning a transcranial magnetic stimulation (TMS) coil with respect to a patient to receive treatment. The device of the invention includes three basic components, each of which is unique to the TMS art. A headset assembly accepts the patient's head and fixes its position, while a coil positioner assembly accepts the headset assembly and holds the headset assembly and the patient's head at a fixed position, controls positioning of the TMS coil within a coordinate system defined about the fixed position, and holds the TMS coil in place at a treatment position during treatment. An alignment strip applied at a position in registration with an anatomical landmark of the patient includes at least one registration mark for aligning the patient's head within the headset assembly. Each of these components working together permit the coil assembly to be located in coordinates with respect to the patient's head such that the treatment may be repeated during a subsequent visit by repeating the coordinates.

In the described exemplary embodiments, the patient's head is held in the headset assembly by quick release straps that permit the patient to be rapidly removed from the headset assembly and the coil positioner assembly in the event of an emergency or the pausing of a treatment. The coil positioner assembly also includes a sighting mechanism that aligns an anatomical landmark of the patient with the coil positioner assembly to define a pivot axis through the patient's nose. For example, the sighting mechanism may include a registration mark that may be aligned with a corner of the patient's eye. The coil positioner assembly may also include a gimbal mount that supports the TMS coil. A counterbalance for the gimbal arrangement and the weight of the coil may also be used to offset the weight that would be applied against the patient's head. The gimbal arrangement may further include a mechanism that adjusts a roll of the TMS coil so that the TMS coil may seat against the patient's head. On the other hand, the coil positioner assembly may include a ball and socket that supports the TMS coil in place of the gimbal mount.

The invention also includes numerous methods of using the elements of the invention to repeatably position a transcranial magnetic stimulation (TMS) coil with respect to a patient to receive treatment. For example, a first method in accordance with the invention comprises the steps of:

fixing the patient's head at a fixed position;
defining a coordinate system about the fixed position;
finding a treatment position on the patient for the TMS coil;
recording the coordinates of the treatment position in the coordinate system; and
mechanically supporting the TMS coil at the treatment position during treatment.

In an exemplary embodiment of this method, the step of fixing the patient's head at a fixed position includes the steps of:

placing the patient's head in a headset assembly having a cushion for accepting a back of the patient's head and alignment straps that restrain the patient's head in the nodding and left/right directions;

applying an alignment strip with a registration mark at a position on the patient so as to align the registration mark with an anatomical landmark of the patient;

wrapping a first of the alignment straps from a back of the patient's head over a crown of the patient's head to an alignment position on the alignment strip; and wrapping a pair of lateral straps of the alignment straps from the back of the patient's head around the respective sides of the patient's head to alignment positions on the alignment strip so as to center the patient's face in the left/right direction in a mid-sagittal plane.

By way of example, the alignment strip may be applied to a forehead of the patient and the registration mark aligned with the patient's nose. In this case, the method may also include the step of adjusting a left/right position of the patient's head until the lateral straps have the same length at the registration mark on the alignment strap.

In accordance with the methods of the invention, the step of finding a treatment position may further comprise the steps of adjusting a first adjustment mechanism so as to adjust an angle of a left or right superior oblique plane with respect to the mid-sagittal plane and adjusting a second adjustment mechanism so as to adjust an anterior/posterior distance in the left or right superior oblique plane. When searching for a motor threshold position, for example, these first and second adjustment mechanisms may be adjusted so as to define a grid pattern of coordinates in respective left superior oblique planes at different angles to the mid-sagittal plane and different positions within each respective left superior oblique plane in an anterior/posterior direction until the treatment position and/or the motor threshold position is found. Once the motor threshold position is found, the treatment position for depression, for example, may be readily found by simply adjusting the second adjustment mechanism in the anterior direction within the left superior oblique plane by 5 cm or a distance that is a function of the size of the patient's head.

In accordance with another aspect of the invention, the step of fixing the patient's head at the fixed position comprises the step of placing the patient's head at an angle with respect to the horizontal that is optimized for patient comfort, cortical excitability, and so as to reduce the weight of the patient's head on the patient's shoulders. In an exemplary embodiment, the angle is approximately 30°-45° from the horizontal.

BRIEF DESCRIPTION OF THE DRAWINGS

The above and other features and advantages will become apparent to those skilled in the art based on the following detailed description of the drawing figures, of which.

DETAILED DESCRIPTION OF ILLUSTRATIVE EMBODIMENTS

A detailed description of an illustrative embodiment of the present invention will now be described with reference to FIGS. 1-5. Although this description provides a detailed example of a possible implementation of the present invention, it should be noted that these details are intended to be exemplary and in no way delimit the scope of the invention.

The present invention is designed to position a TMS coil for treatment of central nervous system disease states using TMS therapies. While an exemplary embodiment of the invention is described with respect to the excitatory stimulation of the left prefrontal cortex for the treatment of depression, those skilled in the art will appreciate that the apparatus and techniques of the invention may be used to apply TMS therapies to many other central nervous system targets for the treatment of numerous other central nervous system diseases. For example, the positioning device of the invention may be used to position the TMS over the right prefrontal cortex of a patient for low frequency inhibitory stimulation in the treatment of depression. Those skilled in the art will further appreciate that the positioning device of the invention also may be used to position a TMS coil for the treatment of: epilepsy (above seizure locus), schizophrenia (at Wernicke's Area), Parkinson's Disease, Tourette's Syndrome, Amyotrophic Lateral Sclerosis (ALS), Multiple Sclerosis (MS), Alzheimer's Disease, Attention Deficit/Hyperactivity Disorder, obesity, bipolar disorder/mania, anxiety disorders (panic disorder with and without agoraphobia, social phobia a.k.a. Social Anxiety Disorder, Acute Stress Disorder, Generalized Anxiety Disorder), Post-traumatic Stress Disorder (one of the anxiety disorders in DSM), obsessive compulsive disorder (one of the anxiety disorders in DSM), pain (migraine, trigeminal neuralgia), chronic pain disorders (including neuropathic pain such as pain due to diabetic neuropathy, post-herpetic neuralgia, and idiopathic pain disorders such as fibromyalgia and regional myofascial pain syndromes), rehabilitation following stroke (neuro plasticity induction), tinnitus, stimulation of implanted neurons to facilitate integration, substance-related disorders (dependence and abuse and withdrawal diagnoses for alcohol, cocaine, amphetamine, caffeine, nicotine, cannabis), spinal cord injury and regeneration/rehabilitation, head injury, sleep deprivation reversal (DARPA), primary sleep disorders (primary insomnia, primary hypersomnia, circadian rhythm sleep disorder), cognitive enhancements, dementias, premenstrual dysphoric disorder (PMS), Drug delivery systems (changing the cell membrane permeability to a drug), induction of protein synthesis (induction of transcription and translation), stuttering, aphasia, dysphagia, essential tremor, Magnetic Seizure Therapy (MST), and other central nervous system disorders that may treated by the application of a magnetic field at particular locations in the brain. Of course, in each case, the treatment positions may vary; however, in each case the positioning device of the invention is useful in finding the treatment location in a repeatable manner and holding the TMS coil in the treatment position during therapy.

Figure 1:
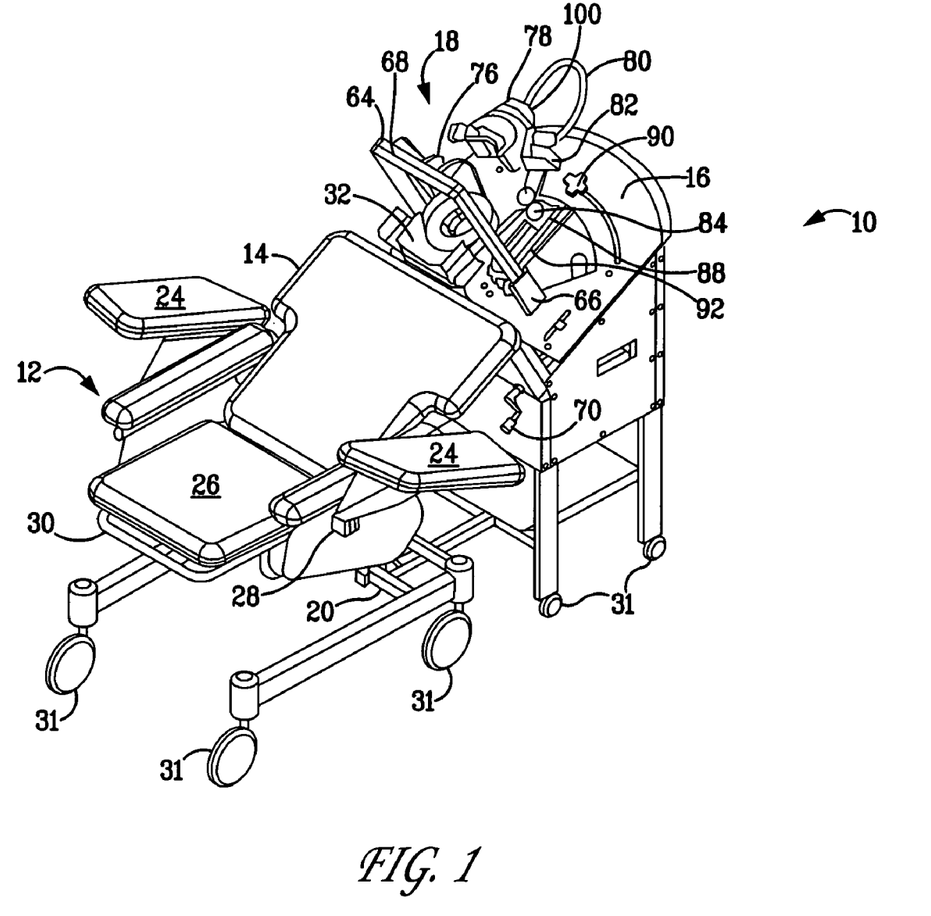
FIG. 1 illustrates a perspective view of the positioner assembly and chair in accordance with an embodiment of the invention.
Figure 2:
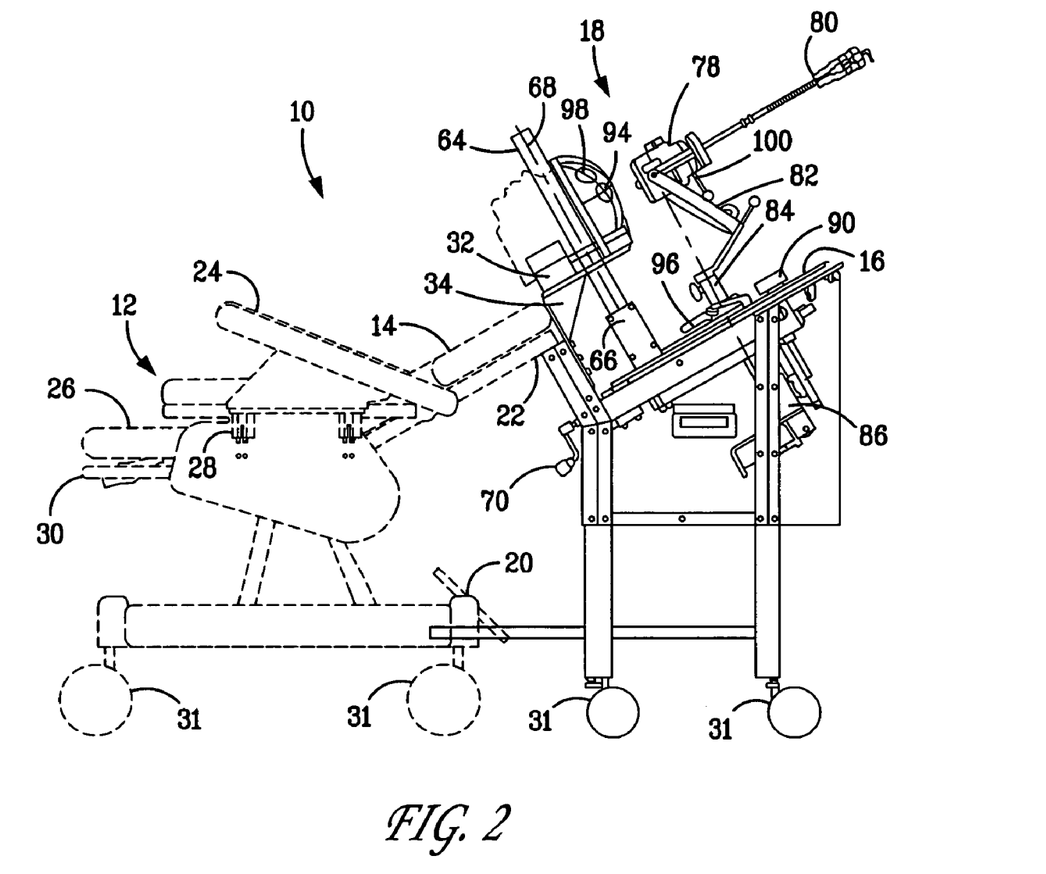
FIG. 2 illustrates a side view of the positioner assembly and chair of FIG. 1 with a patient's head in treatment position.

A perspective view of an exemplary embodiment of the positioner assembly 10 of the invention is illustrated in FIG. 1, while a side view of the positioner assembly 10 of the invention is illustrated in FIG. 2. As illustrated in these figures, the positioner assembly 10 of the invention includes a reclining chair 12 having a back 14 that adjusts so that the patient's head and upper body may lie in a coronal plane parallel to the front plate 16 of the coil positioner assembly 18 during treatment. The coil positioner assembly 18 is locked to the chair frame 20 and the back 14 of the chair 12 is locked in position at 22 as illustrated in FIG. 2. The chair 12 may also include large removable armrests 24 and an adjustable seat cushion 26 to further facilitate patient comfort. Adjustment mechanisms 28, 30 enable adjustment of the chair back 14 and seat cushion 26, respectively. Also, to facilitate movement of the positioner assembly 10 from one treatment room to another, wheels 31 are preferably provided on the chair 12 as well as the coil positioner assembly 18 as indicated.

In an exemplary embodiment, the chair back 14 and the front plate 16 of the coil positioner assembly 18 are at a predetermined angle such as 30°-45° to the horizontal. The actual coronal plane angle is carefully selected to facilitate patient comfort during treatment. Through experimentation, it has been found that an angle of approximately 30°-45° is desired because an angle in this range permits the patient to see around the room during treatment, thereby feeling less vulnerable, which is often an issue with patients undergoing treatment for depression, for instance. The patients also feel more comfortable because such a reclining position is similar to positions during existing TMS treatments, thereby controlling any anxiety over a new treatment apparatus. Also, the 30°-45° angle causes the majority of the weight of the patient's head to rest on the headset assembly, thereby limiting the weight on the patient's shoulders as well as slumping and fidgeting, further increasing patient comfort. Of course, those skilled in the art will appreciate that other angles for the coronal plane may be used as desired, including the horizontal position.

Figure 4:
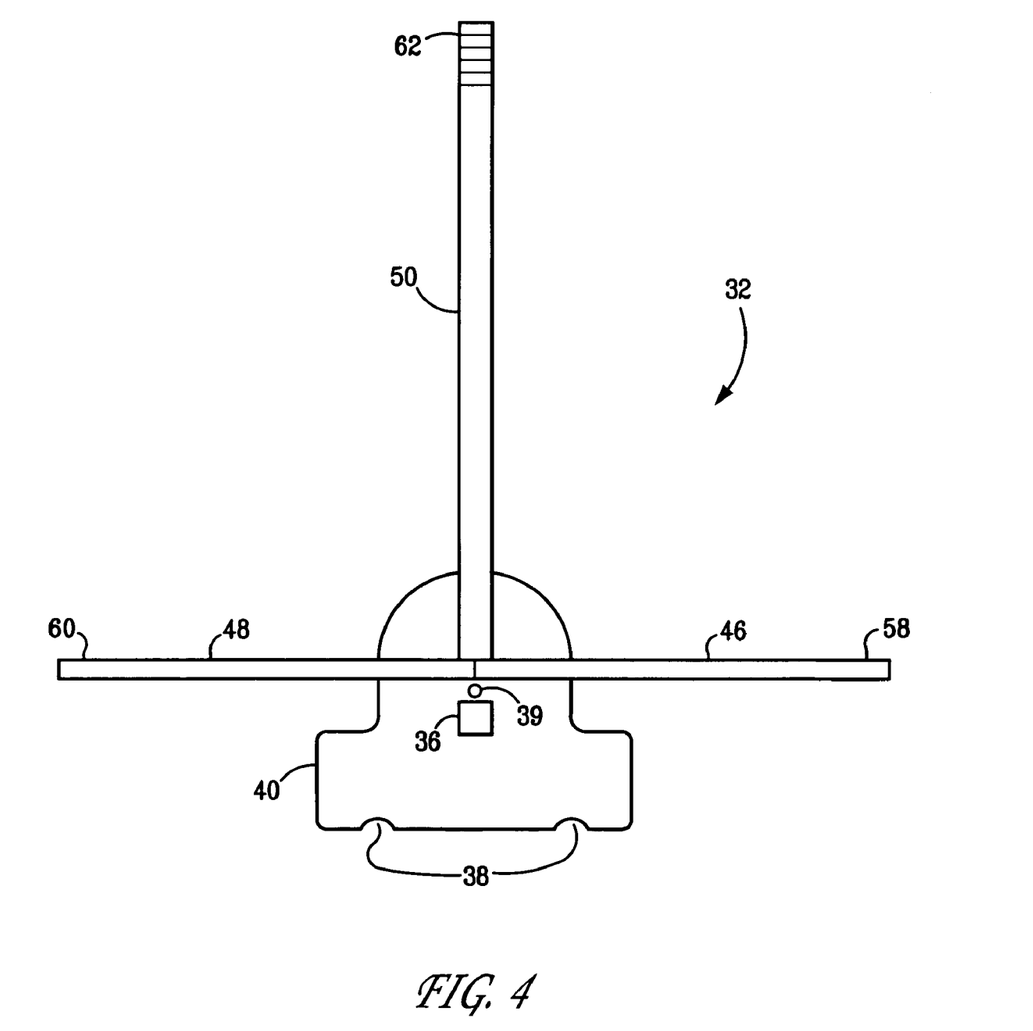
FIG. 4 illustrates a rear view of the disposable headset of FIG. 3.

Once the patient is comfortably seated in the chair 12 and the chair back 14 locked in position in the coronal plane parallel to the front plate 16 of the coil positioner assembly 18, the patient's head is placed in a disposable headset assembly 32 that is removably locked into place on a headrest assembly 34 of the coil positioner assembly 18. In an exemplary embodiment, the headset assembly 32 is removably held in place in a fashion that facilitates quick release in the event that the patient needs to be quickly removed from the treatment apparatus as in an emergency or when the treatment must be paused. For example, a VELCRO™ patch 36 may be provided on the back of the headset assembly 32 as shown in FIG. 4 for mating with a counterpart VELCRO™ patch (not shown) on the headrest assembly 34. Such a disconnect feature preferably allows the patient to be easily rolled onto his or her side in the remote event of seizure. Also, alignment pegs may also be provided on the headrest assembly 34 for accepting alignment notches 38 and/or holes 39 in the base portion 40 (FIG. 4) of the disposable headset assembly 32. The fit of headset assembly 32 onto the headrest assembly 34 is preferably a precise one to enable exact positioning and repositioning of the patient's head.

Figure 3:
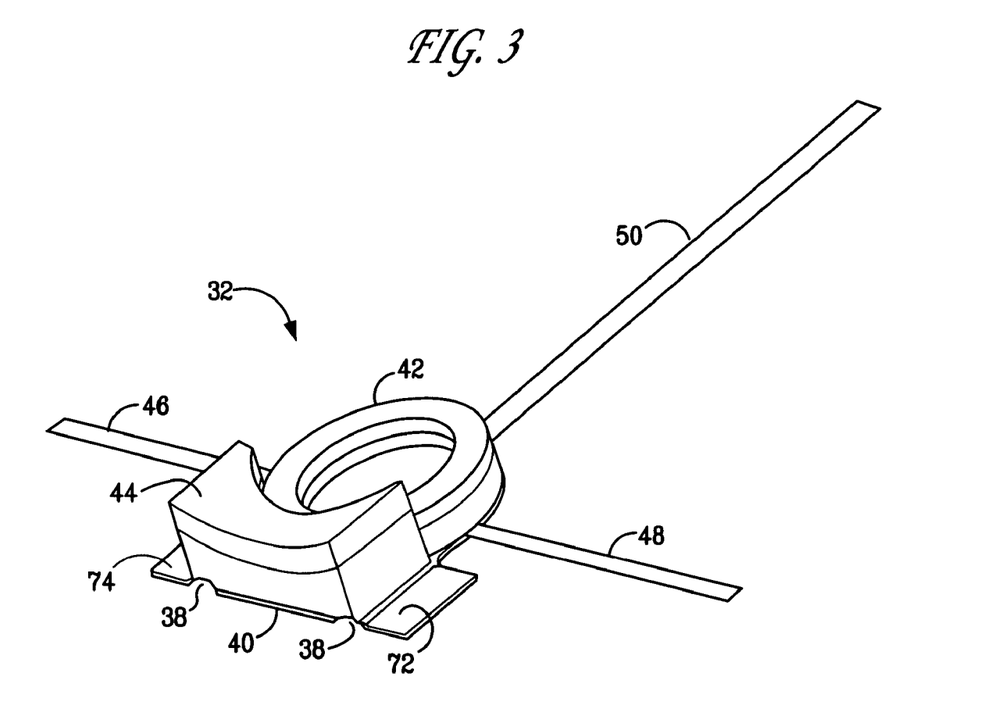
FIG. 3 illustrates a perspective view of the disposable headset placed on the patient's head in accordance with the invention.

FIG. 3 illustrates a perspective view of a disposable headset 32, while FIG. 4 illustrates a rear view of the disposable headset 32. As illustrated, the headset 32 includes cushions 42, 44 that accept and cushion the rear of the patient's head when he/she is reclining in the chair 12 for treatment. During use, the back of the patient's head is rested on the cushion 42 and the patient's neck is rested on cushion 44. Three straps or ribbons 46, 48 and 50 are then used to help align the patient's head in the therapy position. In an exemplary embodiment, these straps are made of TYVEK™ available from DuPont Corporation.

Figure 5:
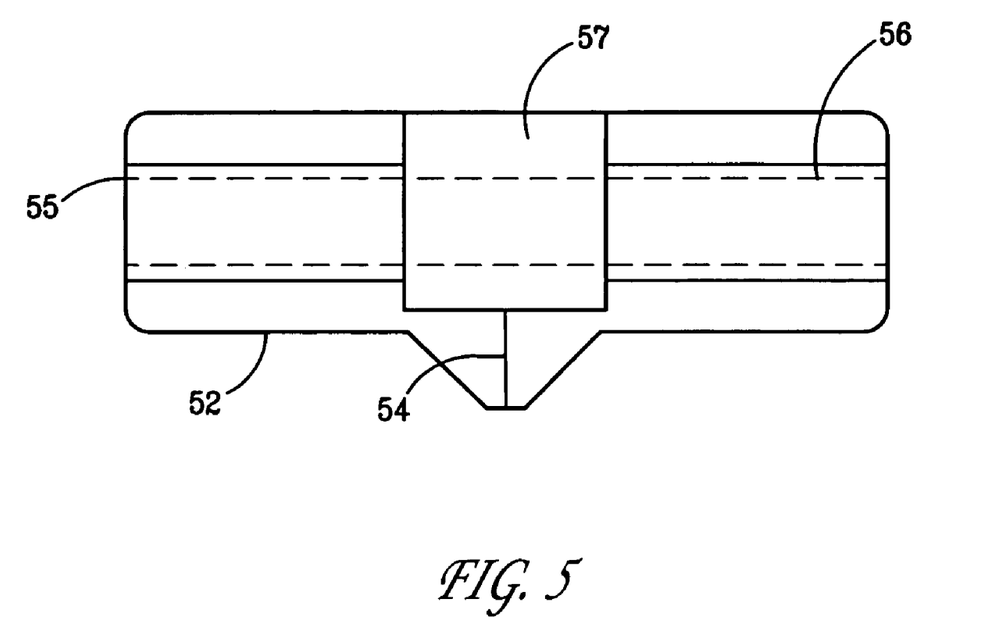
FIG. 5 illustrates the double sided adhesive strip applied to the patient's forehead to provide a registration line with the patient's nose.

To align the patient's head in the therapy position, a disposable double-sided adhesive strip 52 of the type shown in FIG. 5 is applied to the patient's forehead with its center line 54 registered to the center of the patient's nose. This strip is marked in both left/right dimensions at 55, 56 and superior/ inferior dimensions at 57 as shown so that it may serve as a reference coordinate for accepting the straps 46, 48, and 50 and thus allow accurate repositioning of the patient for subsequent therapy sessions. In particular, the patient's head position is adjusted to define a mid-sagittal plane that is perpendicular to the patient's body in a plane through the nose that slices the body into left and right halves. To do this, the lateral straps 46 and 48 are wrapped around from the back of the patient's head to the front. The straps 46, 48 include incremental registration marks 58, 60, respectively, that are gently placed around the patient's temple area and positioned near the forehead strip 52. The head is moved slightly so that the registration marks 58, 60 on each ribbon are equal at the centerline (in other words, the head is centered and not leaning to the left or right). The straps 46, 48 are then cut along the centerline and adhered to the forehead strip 52 at positions 55, 56, respectively, as shown in FIG. 5, thus limiting side to side motion of the patient's head. On the other hand, the straps 46, 48 may be adhered to the forehead strip 52 at positions 55, 56, respectively, and the ends folded back. Alignment in the "nodding axis" of the patient's head is further provided by gently pulling strap 50 snug over the crown of the patient's head and attaching it to forehead strip 52 at position 57 as indicated in FIG. 5 and cutting off or folding back the excess strap. This limits further nodding motion. Registration marks 62 on the strap 50 may be used for this alignment. It should be noted that the adhesion characteristics of the glue on forehead strip 52 are preferably chosen so that the straps 46, 48, and 50 may be easily removed in the event that the patient's head needs to be quickly released from the headset assembly 32.

Once the straps 46, 48, and 50 are applied to the forehead strip 52, a sighting device or alignment guide 64 shaped like an inverted "U" is then placed over the patient's face by inserting respective ends into holders 66 on either side of the patient's head as shown in FIGS. 1 and 2. Sighting device 64 is preferably made of a clear plastic and includes a registration mark 68 that the operator can sight through the sighting device 64 to align to the corner of the patient's eye (lateral canthus) or other anatomical landmark such as eye center (see FIG. 2). The sighting device is adjusted into alignment with the anatomical landmark in the inferior/superior directions by turning a crank 70 that adjusts the sighting device 64 in the inferior/superior directions until the registration mark 68 is aligned with the corner of the patient's eye or other chosen anatomical landmark. Once this adjustment is made, the sighting device 64 is removed and the setting (position) for the sighting device 64 is recorded. In an exemplary embodiment, the setting for the sighting device 64 is recorded on label 72 of the headset assembly 32 as illustrated in FIG. 3. This allows the setting to be linked to the individual patient and his/her headset 32, which is preferably identified by identifying information on label 74. Those skilled in the art will appreciate that a laser or other optical means also could be used to perform this anatomical alignment step. The alignment process to this point takes only approximately a minute.

Once the patient's head is aligned in the headset assembly 32, a stabilizer 76 (FIG. 1) may be pushed up against the side of the patient's head opposite the TMS coil assembly to prevent side-to-side movement of the patient's head when a small force is applied to the other side of the patient's head during the seating of the TMS coil on the patient's head. The patient is now in a fixed and repeatable position about which a cylindrical or other coordinate system (e.g., Cartesian) may be used to guide TMS coil placement. Moreover, a pivot axis has been defined through the center of the patient's nose that is useful in accurately placing the TMS coil assembly. As will be explained below, for the case of excitatory stimulation of the left prefrontal cortex as in the treatment of depression, the mid-sagittal plane through the patient's nose is rotated through this pivot axis to define a left superior oblique plane including the pivot axis in the patient's nose, the motor threshold position (MTP) and therapy position (TXP). Since these points are all defined to be in the same plane, location of the TXP is significantly simplified once the MTP is found. Of course, if other TMS treatments for other central nervous system diseases are being implemented, different treatment positions and planes would be identified and offset with respect to the pivot axis.

The next step is to locate the patient's MTP using established search techniques. In accordance with the invention, the coil assembly 78 with its connector 80 is mounted in a gimbal arrangement 82 supported by an anterior/posterior adjustment post 84 that together fully support the weight of the coil assembly 78 and allow free motion in all axes. In particular, the gimbal arrangement 82 allows for adjustment of the pitch, roll and yaw of the coil assembly 78 for seating of the coil assembly 78 against the patient's head. The gimbal arrangement 82 is placed at an incline perpendicular to the coronal plane (e.g., 30°) and includes a counterbalance 86 to the coil weight (e.g., counter weights, constant force springs, adjustable force cams, and the like) to facilitate easy movement of the gimbal arrangement 82 and anterior/posterior adjustment post 84 in the anterior/posterior direction. In an exemplary embodiment, the counterbalance 86 further helps to counteract the weight of the coil assembly 78 against the patient's head, further increasing the patient's comfort during a therapy session. The gimbal arrangement 82 is further mounted on a turntable 88 that is allowed to move in a plane parallel to the coronal plane to define the angle of the left superior oblique plane projecting through the pivot axis of the patient's nose. The turntable 88 also includes counterbalances to the coil weight (e.g., counter weights, constant force springs, adjustable force cams, and the like) to facilitate easy movement of the gimbal arrangement 82 in the plane parallel to the coronal plane to define a new oblique angle position. The turntable 88 is adjusted by loosening knob 90 and swinging the turntable 88 (and hence the gimbal arrangement 82 and anterior/posterior adjustment post 84) to a different left superior oblique angle with respect to the patient's head. The turntable 88 is positioned so that its lower radial slide 92 (which is loosened to permit the coil assembly 78, gimbal arrangement 82 and anterior/posterior adjustment post to slide toward the patient's head to seat the coil assembly) is on the same plane as the estimated motor threshold position (MTP). For example, the left superior oblique angle may start at 25° and a point selected that is approximately ½ to ⅔ of the distance from the left auditory meatus (i.e. ear canal) to the vertex of the head. The MTP 94 of the patient is then determined through established search techniques by adjusting the position of the radial slide 92 to permit the coil assembly 78 to slide into contact with the patient's head and then searching in a grid about the estimated MTP. In particular, searching is conducted by adjusting the left superior oblique angle in increments by adjusting the angular position of turntable 88 and adjusting anterior (toward nose)/posterior (toward back of head) position by moving the anterior/posterior adjustment post 84 up/down in increments about the estimated MTP position. Once the coil assembly 78 is at the final MTP 94 (e.g., based on sufficient thumb twitching at a grid position found during a patterned search of a grid defined by adjustments of the angle of turntable 88 and the anterior/posterior position of anterior/posterior adjustment post 84), the turntable 88 is locked in place using knob 90 and the anterior/posterior adjustment post 84 is locked in position using knob 96, thereby locking the point of rotation of the positioner assembly 18 in the left superior oblique plane including the patient's nose, the MTP 94 and the treatment position (TXP) 98 for the case of depression treatment. The anterior/posterior setting for the anterior/posterior adjustment post 84 and the left superior oblique angle measurement from turntable 88 are then recorded on label 72 for use in subsequent treatments. The power level for the TMS measurements is also determined at the MTP 94 using known techniques.

All further coil motions will now be in the left superior oblique plane that contains the MTP 92 and the midpoint of the patient's nose. In particular, the TXP 98 for depression treatment is found by moving the coil assembly 78 forward 5 cm in the anterior direction along the oblique plane by adjusting the anterior/posterior adjustment post 84. However, those skilled in the art will appreciate that the distance of the TXP 98 from the MTP 94 may be a function of the head size of the patient. In addition, as noted above, the positioner assembly 10 of the invention could be set up to target any other anatomical landmark of the patient that also produces a repeatable position relative to internal anatomy. For example, rather than searching for the MTP 94 for use in finding a TXP 98 for treating depression, the system of the invention may be used to find the Wernicke's Area for treating schizophrenia or finding other treatment positions for other central nervous system disorders responsive to TMS treatments.

Once the TXP 98 has been found, the next step is to adjust the coil assembly 78 so that it comfortably seats against the patient's head. The gimbal assembly 78 is moved to adjust the pitch and yaw of the coil assembly 78 up against the patient's head. Such adjustments of the gimbal assembly 82 fixes the coil assembly 78 in space without affecting the point of application of the field. The roll of the coil assembly 78 also may be adjusted by turning adjustment knob 100 of the gimbal assembly 82 to adjust any roll in the coil assembly 78 that affects the seating of the coil assembly 78 against the patient's head at the TXP 98. The roll is preferably measured in degrees since a change in orientation with respect to the anatomy in the roll direction may affect the applied magnetic field depending upon the orientation of fold in the patient's brain at the TXP 98. This coil rotation (roll) setting also may be recorded on label 72 of the headset assembly 32. The coil assembly 78 is now at the TXP and ready for patient treatment.

The angular position of the turntable 88 and the anterior/posterior position of anterior/posterior adjustment post 84 are typically indicated with scales; however, the positions may also be indicated using position sensors with position feedback. Use of these measurements in subsequent therapy sessions greatly expedites set up and positioning of the patient. In addition to being recorded on label 72 of the headset assembly 32, these positions also may be automatically read and recorded in digital form using the position sensors with position feedback and the readings processed for inclusion in the patient's record. Position sensors with position feedback may be used for the other adjustments as well. Moreover, the manual adjustments may be made automatically by motor drive units. Of course, the positions also may be manually read and entered by an operator into a medical database containing the patient's medical records.

Since the procedure is highly repeatable, the recorded positions (lateral canthus position, left superior oblique angle, anterior/posterior position, and coil rotation (roll) position) in the patient's coordinates may be used to allow a patient to be treated easily on other systems that employ the same positioning and/or coordinate systems. Moreover, the disposable headset assembly 32 of the invention permits the patient to be repeatably positioned for TMS procedures or other medical procedures on the head.

The present invention is characterized by its ability to provide an alignment plane that includes, for example, the MTP, TXP and midpoint of the nose. The mechanism of the invention establishes such a plane so as to facilitate quick positioning from MTP to TXP. A cylindrical coordinate system aligned with the patient's head is used for such positioning, especially where the cylindrical axis projects through a patient landmark of interest.

Those skilled in the art also will readily appreciate that many additional modifications are possible in the exemplary embodiment without materially departing from the novel teachings and advantages of the invention. For example, the afore-mentioned constant force spring may comprise a rolled coil that applies an equal force in both movement directions to offset the weight of the coil. A pulley system may also be used as a counterweight to gravity in a known fashion.

Those skilled in the art will further appreciate that the manual mechanical adjustments of the invention may be replaced by a manual or electronic articulating arm (e.g., robotic arm) with position feedback and that the coordinates may be read and manipulated using software for recordation. In other words, the software would convert real world coordinates to the coordinate system of the patient and hold the TMS coil in position during treatment.

Also, those skilled in the art will appreciate that the gimbal assembly of the invention may be replaced by a suitable ball and socket arrangement that allows precise control of three-dimensional movements of the coil assembly.

Another significant feature of the invention is its quick release capability. The only thing holding the patient in place is the headset assembly 32, which is connected to the positioner assembly 18 by VELCRO™ and peg alignment with holes and/or slots. The headset assembly 32 thus may be easily removed from the positioner assembly 18 in the unlikely event that the patient has a seizure or treatment needs to be paused for some reason. Moreover, the patient's head may be readily removed from the headset assembly 32 by simply pulling the straps 46, 48, and 50 away from the adhesive on forehead strip 52. Alternatively, a separate headset assembly need not be required. In this case, the positioner assembly 18 could include removable conformal cushions for accepting the patient's head and adjustment straps for aligning the patient's head.

Accordingly, any such modifications are intended to be included within the scope of this invention as defined by the following exemplary claims.

What is claimed:
1. A device comprising:
a transcranial magnetic stimulation coil;
a headset assembly that accepts a patient's head;
a coil positioner assembly configured to hold said headset assembly and the patient's head at a repeatable position, provides a pivot axis through the patient's nose for finding a position used in a treatment procedure, controls positioning of said transcranial magnetic stimulation coil within a coordinate system defined about said repeatable position to find said position used in the treatment procedure, and holds the transcranial magnetic stimulation coil at said position during the treatment procedure.

2. A device as in claim 1, further comprising an alignment strip adapted to be applied to the patient at a position in registration with an anatomical landmark of the patient, said alignment strip including at least one registration mark for aligning the patient's head within said headset assembly.

3. A device as in claim 2, wherein said headset assembly comprises a cushion for accepting a back of the patient's head and alignment straps that restrain the patient's head in the nodding and left/right positions.

4. A device as in claim 3, wherein said alignment strip is aligned with the patient's nose and adapted to be affixed to the patient's forehead to define a mid-sagittal plane, and wherein said alignment straps comprise a crown strap that is adapted to wrap from a back of the patient's head over a crown of the patient's head to an alignment position on the alignment strip and a pair of lateral straps that are adapted to wrap from the back of the patient's head around the respective sides of the patient's head to alignment positions on the alignment strip so as to center the patient's face in the left/right direction in the mid-sagittal plane.

5. A device as in claim 4, wherein the lateral straps each include registration marks that register the headset assembly with respect to said alignment strip.

6. A device as in claim 3, wherein said alignment straps releasably connect to said alignment strip to permit the patient to be rapidly removed from the headset assembly and the coil positioner assembly in the event of an emergency or the pausing of a treatment.

7. A device as in claim 6, wherein said headset assembly is releasably attached to said coil positioner assembly.

8. A device as in claim 1, wherein the headset assembly includes a recording label upon which coordinates of said position used in the treatment procedure with respect to said repeatable position may be recorded.

9. A device as in claim 1, further including a chair that accepts the patient and locks to said coil positioner assembly at a predetermined angle so as to fix a position of said headset assembly with respect to said coil positioner assembly and a coronal plane for the patient's head.

10. A device as in claim 9, wherein said predetermined angle is in a range of approximately 30°-45°.

11. A device as in claim 1, wherein said coil positioner assembly includes a robotic alignment arm that moves said transcranial magnetic stimulation coil to the position used in the treatment procedure and supports said transcranial magnetic stimulation coil at the position used in the treatment procedure.

12. A device comprising:
a transcranial magnetic stimulation coil;
a headset assembly that accepts a patient's head; and
a coil positioner assembly configured to hold said headset assembly and the patient's head at a repeatable position, controls positioning of said transcranial magnetic stimulation coil within a coordinate system defined about said repeatable position, and holds the transcranial magnetic stimulation coil at a position used in a treatment procedure, wherein said coil positioner assembly includes a first adjustment mechanism that adjusts the position of said transcranial magnetic stimulation coil relative to said repeatable position in a direction parallel to a mid-sagittal plane through the patient, a second adjustment mechanism that adjusts said transcranial magnetic stimulation coil in a direction of an angle of a left superior oblique plane that includes a pivot axis through a nose of the patient, a motor threshold position in the patient's head, and said position used in the treatment procedure with respect to said mid-sagittal plane, and a third adjustment mechanism that adjusts an anterior/posterior distance of said transcranial magnetic stimulation coil in said superior oblique plane.

13. A device as in claim 12, wherein said coil positioner assembly further comprises at least one position recording element that records a location of the position used in the treatment procedure of said transcranial magnetic stimulation coil in said coordinate system relative to said repeatable position, said location being identified by respective settings of said first, second and third adjustment mechanisms.

14. A device comprising:
a transcranial magnetic stimulation coil;
a headset assembly that accepts a patient's head; and
a coil positioner assembly configured to hold said headset assembly and the patient's head at a repeatable position, controls positioning of said transcranial magnetic stimulation coil within a coordinate system defined about said repeatable position, and holds the transcranial magnetic stimulation coil at a position used in a treatment procedure, wherein said coil positioner assembly includes a gimbal arrangement that supports said transcranial magnetic stimulation coil and a counterbalance for said gimbal arrangement.

15. A device as in claim 14, wherein said counterbalance comprises at least one of a counterweight, at least one constant force spring, and an adjustable force cam.

16. A device as in claim 14, wherein said gimbal arrangement includes a mechanism that adjusts a roll of the transcranial magnetic stimulation coil so that said transcranial magnetic stimulation coil may seat against the patient's head.

17. A device comprising:
a transcranial magnetic stimulation coil;
a headset assembly that accepts a patient's head; and
a coil positioner assembly configured to hold said headset assembly and the patient's head at a repeatable position, controls positioning of said transcranial magnetic stimulation coil within a coordinate system defined about said repeatable position, and holds the transcranial magnetic stimulation coil at a position used in a treatment procedure, wherein said coil positioner assembly includes a ball and socket that supports said transcranial magnetic stimulation coil.

18. A coil positioner assembly comprising:
a transcranial magnetic stimulation coil;
a headrest assembly configured to hold the patient's head at a repeatable position; and
positioning apparatus that positions said transcranial magnetic stimulation coil within a coordinate system defined about said repeatable position and holds the transcranial magnetic stimulation coil at a position used in a treatment procedure, wherein said positioning apparatus includes a first adjustment mechanism that adjusts the position of said transcranial magnetic stimulation coil relative to said repeatable position in a direction parallel to a mid-sagittal plane through the patient, a second adjustment mechanism that adjusts said transcranial magnetic stimulation coil in a direction of an angle of a left superior oblique plane that includes a pivot axis through a nose of the patient, a motor threshold position in the patient's head, and said position used in the treatment procedure with respect to said mid-sagittal plane, and a third adjustment mechanism that adjusts an anterior/posterior distance of said transcranial magnetic stimulation coil in said superior oblique plane.

19. An assembly as in claim 18, wherein said positioning apparatus further comprises at least one position recording element that records a location of the positions used in the treatment procedure of said transcranial magnetic stimulation coil in said coordinate system relative to said repeatable position, said location being identified by respective settings of said first, second and third adjustment mechanisms.

20. An assembly as in claim 18, further including a chair that accepts the patient and locks to said headrest assembly at a predetermined angle so as to fix a position of said headset assembly with respect to said positioning apparatus and a coronal plane for the patient's head.

21. An assembly as in claim 20, wherein said predetermined angle is in a range of approximately 30°-45°.

22. A coil positioner assembly comprising:
a transcranial magnetic stimulation coil;
a headrest assembly configured to fix the patient's head at a fixed left/right position so as to define a mid-sagittal plane through the patient's nose;
a positioning apparatus that positions said transcranial magnetic stimulation coil with respect to the mid-sagittal plane and holds the transcranial magnetic stimulation coil at a position used in a treatment procedure; and
a sighting mechanism including a registration mark configured to align a corner of the patient's eye with the positioning apparatus to define a pivot axis through the patient's nose for finding the position used in the treatment procedure.

23. A coil positioner assembly comprising:
a transcranial magnetic stimulation coil;
a headrest assembly configured to hold the patient's head at a repeatable position; and
positioning apparatus that positions said transcranial magnetic stimulation coil within a coordinate system defined about said repeatable position and holds the transcranial magnetic stimulation coil at a position used during a treatment procedure, wherein said positioning apparatus includes a gimbal arrangement that supports said transcranial magnetic stimulation coil and a counterbalance for said gimbal arrangement.

24. An assembly as in claim 23, wherein said counterbalance comprises at least one of a counterweight, at least one constant force spring, and an adjustable force cam.

25. An assembly as in claim 23, wherein said gimbal arrangement includes a mechanism that adjusts a roll of the transcranial magnetic stimulation coil so that said transcranial magnetic stimulation coil may seat against the patient's head.

26. A coil positioner assembly comprising:
a transcranial magnetic stimulation coil;
a headrest assembly configured to hold the patient's head at a repeatable position;
positioning apparatus that positions said transcranial magnetic stimulation coil within a coordinate system defined about said repeatable position and holds the transcranial magnetic stimulation coil at a position used in a treatment procedure, wherein said positioning apparatus includes a ball and socket that supports said transcranial magnetic stimulation coil.

27. An assembly as in claim 22, wherein said positioning apparatus includes a robotic alignment arm that moves said transcranial magnetic stimulation coil to the position used during the treatment procedure and supports said transcranial magnetic stimulation coil at the position used during the treatment procedure.

28. A method for repeatably positioning a transcranial magnetic stimulation coil with respect to a patient to receive treatment, comprising the steps of:
placing the patient's head in a headset assembly having a cushion for accepting a back of the patient's head and alignment straps that restrain the patient's head in the nodding and left/right directions;
applying an alignment strip with a registration mark at a position on the patient so as to align the registration mark with an anatomical landmark of the patient;
wrapping a first of said alignment straps from a back of the patient's head over a crown of the patient's head to an alignment position on the alignment strip;
wrapping a pair of lateral straps of said alignment straps from the back of the patient's head around the respective sides of the patient's head to alignment positions on the alignment strip so as to center the patient's face in the left/right direction in a mid-sagittal plane;
defining a coordinate system about the patient's head;
finding a position used in a treatment procedure on the patient for the transcranial magnetic stimulation coil;
recording the coordinates of the position used in the treatment procedure in said coordinate system; and
mechanically supporting the transcranial magnetic stimulation coil at the position used in the treatment procedure.

29. A method as in claim 28, wherein said alignment strip is applied to a forehead of the patient and said registration mark is aligned with the patient's nose, said lateral straps wrapping step comprising the step of adjusting a left/right position of the patient's head until said lateral straps have the same length at the registration mark on the alignment strap.

30. A method as in claim 28, wherein said wrapping steps comprise the step of releasably connecting said first alignment strap and said pair of lateral straps to said alignment strip to permit the patient to be rapidly removed from the headset assembly in the event of an emergency or the pausing of a treatment.

31. A method as in claim 28, wherein said mechanically supporting step comprises the step of placing the transcranial magnetic stimulation coil in a gimbal arrangement that is movable in said coordinate system.

32. A method as in claim 28, further comprising the step of placing the patient's head at an angle with respect to the horizontal that is optimized for patient comfort, cortical excitability, and so as to reduce the weight of the patient's head on the patient's shoulders.

33. A method as in claim 31, wherein said mechanically supporting step comprises the additional step of adjusting a roll of the transcranial magnetic stimulation coil in said gimbal arrangement so that said transcranial magnetic stimulation coil may seat against the patient's head.

34. A method as in claim 32, wherein said angle is in a range of approximately 30°-45° from the horizontal.

35. A method for repeatably positioning a transcranial magnetic stimulation coil with respect to a patient to receive treatment, comprising the steps of:
aligning a registration mark of a sighting mechanism with a corner of a patient's eye so as to define a pivot axis through the patient's nose;
defining a coordinate system about the patient's head;
finding a position used in a treatment procedure on the patient with respect to the pivot axis for the transcranial magnetic stimulation coil;
recording the coordinates of the position used in the treatment procedure in said coordinate system; and
mechanically supporting the transcranial magnetic stimulation coil at the position used in the treatment procedure.

36. A method as in claim 35, wherein said coordinates recording step comprises the step of recording a position at which said registration mark of said sighting mechanism is aligned with a corner of the patient's eye.

37. A method for repeatably positioning a transcranial magnetic stimulation coil with respect to a patient to receive treatment, comprising the steps of:
- placing the patient's head at a repeatable position;
- defining a coordinate system about the repeatable position;
- finding a position used in a treatment procedure by adjusting a first adjustment mechanism so as to adjust an angle of a superior oblique plane with respect to a mid-sagittal plane and adjusting a second adjustment mechanism so as to adjust an anterior/posterior distance in said superior oblique plane;
- recording the coordinates of the position used in the treatment procedure in said coordinate system; and
- mechanically supporting the transcranial magnetic stimulation coil at the position used during the treatment procedure.

38. A method as in claim 37, comprising the step of alternately adjusting said first and second adjustment mechanisms so as to define a grid pattern of coordinates in respective superior oblique planes at different angles to the mid-sagittal plane and different positions within each respective superior oblique plane in an anterior/posterior direction until one of said position used in the treatment procedure and an indicator of said position used in the treatment procedure is found.

39. A method as in claim 37, wherein said coordinates recording step comprises the step of recording a location of the position used in the treatment procedure of said transcranial magnetic stimulation coil in said coordinate system relative to said repeatable position as respective settings of said first and second adjustment mechanisms.

40. A method as in claim 37, wherein said steps of adjusting the first and second adjustment mechanisms and recording the coordinates of the position used in the treatment procedure include the steps of automatically moving the transcranial magnetic stimulation coil and automatically recording the position used in the treatment procedure from readings of position sensors.

41. A method as in claim 39, wherein said step of placing the patient's head at said repeatable position comprises the step of placing the patient's head in a disposable headset assembly, and wherein said coordinates recording step comprises the step of recording said respective settings of said first and second adjustment mechanisms on a label of said disposable headset.

42. A method for repeatably positioning a transcranial magnetic stimulation coil with respect to a patient to receive treatment, comprising the steps of:
- placing the patient's head at a repeatable position;
- defining a coordinate system about the repeatable position;
- finding a position used in a treatment procedure on the patient for the transcranial magnetic stimulation coil;
- recording the coordinates of the position used in the treatment procedure in said coordinate system; and
- mechanically supporting the transcranial magnetic stimulation coil at the position used in the treatment procedure, including applying a counterbalance to the transcranial magnetic stimulation coil so as to reduce a weight force applied against the patient by the transcranial magnetic stimulation coil during the treatment procedure.

43. A method for repeatably positioning a transcranial magnetic stimulation coil with respect to a patient to receive treatment, comprising the steps of:
- fixing the patient's head at a fixed left/right position so as to define a mid-sagittal plane through the patient's nose;
- aligning a sighting mechanism with an anatomical landmark of the patient so as to define a pivot axis through the patient's nose; and
- adjusting the transcranial magnetic stimulation coil with respect to the mid-sagittal plane and the pivot axis to find a position used in a treatment procedure.

44. A method as in claim 43, wherein said aligning step includes the step of aligning a registration mark of said sighting mechanism with a corner of the patient's eye.

45. A method as in claim 43, comprising the step of removing the sighting mechanism once the pivot axis is defined.

* * * * *

UNITED STATES PATENT AND TRADEMARK OFFICE
CERTIFICATE OF CORRECTION

PATENT NO. : 7,651,459 B2 Page 1 of 1
APPLICATION NO. : 10/752164
DATED : January 26, 2010
INVENTOR(S) : Cameron et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 924 days.

Signed and Sealed this

Twenty-eighth Day of December, 2010

David J. Kappos
*Director of the United States Patent and Trademark Office*